United States Patent [19]

Liao et al.

[11] Patent Number: 5,439,950
[45] Date of Patent: Aug. 8, 1995

[54] WATER MISCIBLE NON-HYDROLYZABLE CROSS-LINKERS AND HIGH REFRACTIVE INDEX HYDROGELS PREPARED THEREWITH

[75] Inventors: Xiugao Liao, Alhambra; Yading Wang, Pasadena; Stephen O. Zhou, Hacienda Heights, all of Calif.; Thomas P. Richards, Shelton, Wash.

[73] Assignee: Kabi Pharmacia Ophthalmics, Inc., Monrovia, Calif.

[21] Appl. No.: 266,951

[22] Filed: Jun. 27, 1994

[51] Int. Cl.⁶ .................. C08F 226/06; A61L 27/00
[52] U.S. Cl. .................... 523/108; 523/113; 524/548; 526/257; 526/258; 526/262; 526/263; 544/242; 544/336; 548/335.1
[58] Field of Search ........... 523/108, 113; 524/548; 526/257, 258, 262, 263; 544/242, 336; 548/335.1

[56] References Cited

U.S. PATENT DOCUMENTS

| | | | |
|---|---|---|---|
| 3,361,858 | 1/1968 | Wichterle | 264/1 |
| 4,182,802 | 1/1980 | Loshaek | 526/263 |
| 4,556,998 | 12/1985 | Siepser | 623/6 |
| 4,573,998 | 3/1986 | Mazzocco | 623/6 |
| 4,731,079 | 3/1988 | Stoy | 623/6 |
| 4,743,254 | 5/1988 | Davenport | 623/6 |
| 4,808,182 | 2/1989 | Barrett | 623/6 |
| 4,813,954 | 3/1989 | Siepser | 623/6 |
| 4,833,890 | 5/1989 | Kelman | 623/6 |
| 4,911,714 | 3/1990 | Poley | 623/6 |
| 4,919,662 | 4/1990 | Knoll et al. | 623/6 |
| 4,936,850 | 6/1990 | Barrett | 623/6 |
| 4,993,936 | 2/1991 | Siepser | 425/408 |
| 4,997,442 | 3/1991 | Barrett | 623/6 |
| 5,147,394 | 9/1992 | Siepser et al. | 623/6 |
| 5,201,763 | 4/1993 | Brady et al. | 623/6 |
| 5,210,111 | 5/1993 | Goldenberg et al. | 523/108 |
| 5,217,491 | 6/1993 | Vanderbilt | 623/6 |

FOREIGN PATENT DOCUMENTS

| | | |
|---|---|---|
| 197325 | 9/1987 | Japan . |
| 2114578 | 6/1980 | United Kingdom . |

OTHER PUBLICATIONS

Dreifus et al., "Intracameral Lenses Made of Hydrocolloidal Acrylates", *Ceskoslovenska oftalmologie*, undated, vol. 16, No. 2, p. 1860.

Packard et al., "Poly-HEMA as a material for intraocular lens implantation: a preliminary report", *British Journal of Ophthalmology*, 1981, 65, 585–587.

*Primary Examiner*—David Buttner
*Attorney, Agent, or Firm*—Poms, Smith, Lande & Rose

[57] ABSTRACT

Non-hydrolyzable, hydrophilic, heterocyclic cross-linking agents for cross-linking vinyl comonomers are provided. The cross-linked copolymers form optically transparent, high water content, and high refractive index hydrogels having long term stability which are useful as intraocular lenses and superabsorbents. The crosslinkers are selected from 4,6 divinyl pyrimidine, 2,5 divinyl pyrazine, 1,4 divinyl imidazole and 1,5 divinyl imidazole.

9 Claims, 2 Drawing Sheets

WATER MISCIBLE NON-HYDROLYZABLE CROSS-LINKERS AND HIGH REFRACTIVE INDEX HYDROGELS PREPARED THEREWITH

BACKGROUND OF THE INVENTION

1. Field of the Invention

The present invention relates generally to cross-linking agents. More particularly, this invention relates to cross-linkers which can be used to provide high water content, optically transparent, high refractive index hydrogels which are especially useful in the fabrication of intraocular lenses. In one of its more particular aspects, this invention relates to methods for the synthesis of such cross-linkers. In another of its more particular aspects, the present invention relates to hydrogels prepared utilizing such cross-linkers.

2. Description of Related Art

Since the early 1940s, optical devices in the form of intraocular lenses have been utilized to replace the natural physiological crystalline ocular lens in humans and other mammals. Typically, the intraocular lens is implanted within the ocular environment immediately after surgically removing the natural lens which has become opaque or otherwise damaged by cataract formation or injury.

For decades the most prevalently utilized materials for forming intraocular lenses were acrylates or methacrylates and particularly polymethylmethacrylate, a rigid, glassy polymer. However, since full-size polymethylmethacrylate intraocular lenses have diameters in the range of 8-13 mm, relatively large incisions were necessary in order to remove the natural lens and insert the intraocular lens.

Recently developed surgical techniques and improved instrumentation have made it possible to remove the opaque or damaged natural lens through incision sizes as small as 2-3 mm. Because small incision surgery is much less traumatic for patients and decreases complications and healing time, this technique has become the method of choice for a large number of ophthalmic surgeons.

A number of different intraocular lens designs and materials have been developed for use in connection with small incision surgical techniques. One approach utilizes the concept of preparing lenses from elastomeric materials such as silicones and thermoplastic polymers. Prior to surgically inserting the elastomeric lens, the surgeon rolls or folds the lens so that it is reduced in size for passing into the eye through a smaller incision. Once placed within the eye, the lens unfolds or unrolls to its full size.

One problem associated with these elastomeric lenses is the possibility that permanent deformation or crease marks may occur when the lens is folded or rolled. This is especially a concern at the center of the lens optical zone where most of the rolling or folding deformation takes place.

Another approach to providing a small incision intraocular lens is suggested in U.S. Pat. No. 4,731,079. This reference discloses an intraocular lens formed of a polymer having a softening (or glass transition) temperature less than 42° C. and preferably about body temperature. The lens can be heated to above its softening temperature and deformed by compression or elongation to reduce at least one dimension. Then, by cooling the lens at a temperature substantially below its softening temperature, the lens will remain in the deformed configuration until it is warmed. Ophthalmic surgeons can implant the deformed lens and once the lens warms to body temperature it returns to its original configuration. A major problem associated with these intraocular lenses is the restricted number of polymers available for preparing the lenses. Polymethylmethacrylate has a glass transition temperature of 100° C. and thus cannot be used to form these lenses. Most acrylates and methacrylates have similarly high glass transition temperatures. Though formulating the lenses with plasticizers will lower the glass transition temperature, the presence of plasticizers in intraocular lenses is generally unacceptable to most surgeons because of potential leaching problems. Alternatively, water is a suitable plasticizer. However, only small amounts of water, typically less than 10%, can be utilized in the polymers to place the glass transition in the appropriate range. Thus, typical hydrogels which have much higher amounts of water are not suitable for fabricating the deformable lenses.

An additional drawback with this suggested small incision intraocular lens is the added degree of surgical complexity required to deform the lens into its small incision configuration. The lenses disclosed in U.S. Pat. No. 4,731,079 are packaged in a form that requires the implanting surgeon to warm, deform, and cool the lens immediately prior to its implantation. This procedure is considerably more involved than traditional lens implantation techniques.

Another suggested approach for small incision lens implantation involves implanting hydrogel intraocular lenses in their smaller dehydrated state. Once the implanted dehydrated lens is secured within the eye it reportedly hydrates and swells in the aqueous ocular environment. A significant problem associated with this approach is the large amount of swelling required to produce an effective lens diameter. In order to fully swell the lens from a diameter of about 3 mm to about 6 mm the lens must swell 8 times by volume. This translates to a lens which is about 85% water. For larger full sized intraocular lenses the swell volume is much higher. Since most hydrogels are structurally very weak at these high water contents, many surgeons are reluctant to implant them. Also, these high water content hydrogels have a very low refractive index, $n_D^{20}$, of around 1.36. In order to achieve suitable refractive powers, the hydrogel lens must therefore be thicker in the optic portion. As a result, a dehydrated hydrogel intraocular lens that will fit through a desirably small incision will not swell to a sufficiently large hydrated size to effectively function as an intraocular lens. This problem is compounded if larger, full size intraocular lenses that have optic diameters greater than 6 mm are desired. In order to produce a hydrated lens having a sufficient optic diameter the dehydrated hydrogel lens must be larger than desirable for a small incision implantation procedure. Alternatively, U.S. Pat. No. 4,919,662 suggests rolling or folding hydrogel intraocular lenses in their elastic hydrated form, and then dehydrating the lenses at lower temperatures to fix the rolled or folded lens configuration at a size suitable for small incision implantation. Once implanted, these lenses hydrate and swell to the original lens configuration. This method has the disadvantage of requiring the handling of fully hydrated lenses during the deforming process. Unfortunately, hydrated lenses have relatively weak tear strengths and handling the lenses causes frequent tearing damage.

U.S. Pat. No. 4,813,954 discloses expansile hydrogel intraocular lenses which are formed by simultaneously deforming and dehydrating hydrogel intraocular lenses prior to implanting the lenses in their dehydrated state. Lenses subjected to this treatment swell to about 180% of their reduced size. For example, lenses deformed or compressed to a diameter of 3.2 mm will swell to only about 5.8 mm. Thus, while providing some advantages over simply implanting dehydrated lenses, the method and lenses described in U.S. Pat. No. 4,813,954 do not result in full sized implanted intraocular lenses of over 8 mm.

In addition to size considerations, however, the constitution of the hydrogels must also be considered. The provision of high water content, optically transparent, high refractive index hydrogels which possess long term stability depends to a large extent upon the make-up of the hydrogel. Since most hydrogels are composed of cross-linked copolymers, the selection of appropriate comonomers is an important consideration. Moreover, whether a hydrogel will be satisfactory for a particular application also depends upon the suitability of the cross-linking agent utilized in the production of the hydrogel.

Many conventional cross-linkers are hydrophobic materials, the use of which in hydrogels reduces the water content thereof. Hydrophobic cross-linkers, in addition, may cause microphase separation in the hydrogels in which they are used, resulting in cloudy hydrogels, rather than the optically transparent hydrogels desired for many applications.

Hydrophilic cross-linkers, a number of which are commercially available, possess advantages over hydrophobic cross-linkers with respect to hydrogel water content and optical transparency. However, since known hydrophilic cross-linkers generally contain ester or amide linkages, they are subject to hydrolysis, which can adversely affect the long-term stability of the hydrogels in which they are used. Hydrolysis of the ester or amide linkages of the cross-linker promotes polymer chain scission leading to hydrogel degradation.

In general, presently available cross-linkers fall into one of two classes. They are either non-hydrolyzable, hydrophobic cross-linkers or hydrolyzable, hydrophilic cross-linkers. Since both classes of cross-linkers have disadvantages, a compromise must frequently be reached based upon the specific application for the hydrogel in which the cross-linker is used. For certain more demanding applications, however, neither class of cross-linkers is totally satisfactory, since, for optimum utilization, the cross-linker must be both non-hydrolyzable and hydrophilic.

It is therefore an object of the present invention to provide cross-linkers which are both non-hydrolyzable and hydrophilic.

Another object of this invention is to provide methods for the synthesis of such cross-linkers.

An additional object of this invention is to provide cross-linked hydrogels having the properties of high water content, high refractive index, optical transparency, and long term stability.

Other objects and advantages of the present invention will become apparent from the following disclosure and description.

SUMMARY OF THE INVENTION

The present invention accomplishes the above-mentioned objectives by providing a series of novel cross-linking agents for hydrophilic polymers, which cross-linking agents are both non-hydrolyzable and hydrophilic. The novel cross-linking agents are carbon-substituted divinyl heterocyclic compounds in which the heterocyclics contain two nitrogen atoms. These novel compounds are exemplified by 4,6-divinylpyrimidine and 2,5-divinylpyrazine. In addition to being hydrophilic and non-hydrolyzable, these compounds have high refractive indices. The refractive index of 4,6-divinylpyrimidine is 1.569, and the refractive index of 2,5-divinylpyrazine is 1.595. Other divinyl heterocyclic compounds which can be used as hydrophilic non-hydrolyzable cross-linkers include a mixture of 1,4-divinylimidazole and 1,5-divinylimidazole, the refractive index of which is 1.560.

The novel compounds, 4,6-divinylpyrimidine and 2,5-divinylpyrazine, can be synthesized using the corresponding dimethyl compound as the starting material. The process consists of two reactions, in the first of which the methyl groups are converted to dimethylaminoethyl groups and, in the second of which, the dimethylaminoethyl groups are converted to vinyl groups by alkylation and deamination.

Hydrogels prepared using the cross-linkers of the present invention with hydrophilic copolymers have the desirable properties of high water content, high refractive index, optical transparency, and long term stability.

Exemplary hydrogel-forming materials suitable for use in the present invention include any polymer, copolymer, or polymer blend which is biocompatible and hydrates to a hydrogel having a hydrated equilibrium water content of at least 20%. Such materials include copolymers formed of at least one hydrophilic or water soluble monomer and one hydrophobic monomer. Particularly preferred are cross-linked polymers and copolymers of heterocyclic, aromatic compounds such as 3-vinylpyridine, 4-vinylpyridine, 4-vinylpyrimidine, vinylpyrazine, and 2-methyl-5-vinylpyrazine. Copolymers of two or more of these comonomers or copolymers of one or more of these comonomers with N-vinylimidazole, 4-methyl-5-vinylthiazole, N-vinylpyrrolidone, or other non-aromatic heterocyclic compounds when cross-linked with the cross-linkers of the present invention have refractive indices, $n_D{}^{20}$, ranging from 1.54 to 1.6 in the dry state. They hydrate to a hydrated equilibrium water content ranging from about 40% to 90%.

The relative amounts of the various comonomers used to produce the hydrogel-forming materials will depend upon the desired final water content, the desired refractive index, and the amount of material elasticity required to deform a lens fabricated of the hydrogel. The hydrogel materials also should have sufficient resiliency at their deformation temperatures to prevent permanent stretching or cracking during or after any deforming process.

Use of the cross-linkers of the present invention assures the provision of cross-linked polymers and copolymers which have the properties desired for use in a wide variety of applications, especially those applications requiring high hydrophilicity and long term stability. For example, the hydrogels prepared using the cross-linkers of the present invention can be used to produce polyelectrolyte gels and high water content superabsorbents, intraocular lenses, contact lenses, cornea on-lays, cornea in-lays, and other medical devices requiring these properties. Hydrogel materials prepared using the cross-linkers of the present invention display higher water content and superior optical clarity compared to non-hydrolyzable but hydrophobic cross-linkers such as divinyl benzene, or hydrophilic but hydrolyzable cross-linkers such as diethylene glycol diacrylate and allyl methacrylamide. Hydrogels prepared using the cross-linkers of the present invention are also observed to have considerably more stability over an extended period of time than hydrogels prepared using previously available cross-linkers. Intraocular lenses, for example, made from hydrogel materials utilizing the cross-linkers of the present invention showed excellent optical resolution, good water content, excellent shape recovery, and long term stability.

Further objects, features and advantages of the cross-linkers and hydrogels of the present invention, as well as a better understanding thereof, will be afforded to those skilled in the art from a consideration of the following detailed explanation of exemplary embodiments thereof when taken in connection with the accompanying drawings.

DETAILED DESCRIPTION OF THE EXEMPLARY EMBODIMENTS

The present invention provides novel compounds which are useful for cross-linking hydrophilic polymeric materials. The novel cross-linkers can be characterized as heterocyclic compounds containing a multiplicity of vinyl groups. In particular, the compounds are heterocyclic nitrogen compounds containing two nitrogen atoms in which the vinyl groups are attached to carbon atoms of the heterocyclic ring. These novel compounds are exemplified by 4,6-divinylpyrimidine, the structural formula of which is shown in FIG. 1, and by 2,5-divinylpyrazine, the structural formula of which is shown in FIG. 2.

Figure 1:
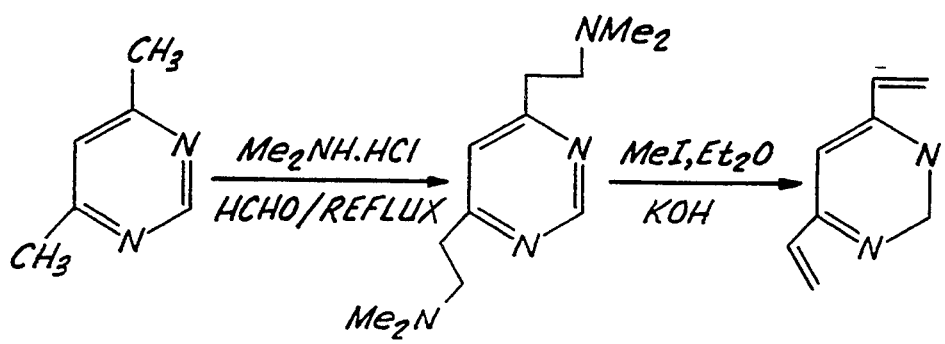
FIG. 1 illustrates a synthetic scheme for the preparation of 4,6-divinylpyrimidine, one of the novel cross-linkers of the present invention.

The compound 4,6-divinylpyrimidine is miscible with water and can be prepared according to the synthetic scheme illustrated in FIG. 1. As shown, in a two-step process, 4,6-dimethylpyrimidine is reacted with dimethylamine hydrochloride and formaldehyde to provide the corresponding 4,6-bis(dimethylaminoethyl)pyrimidine. This dimethylaminoethyl compound is methylated and deaminated in the presence of a base to provide the desired 4,6-divinylpyrimidine.

Figure 2:
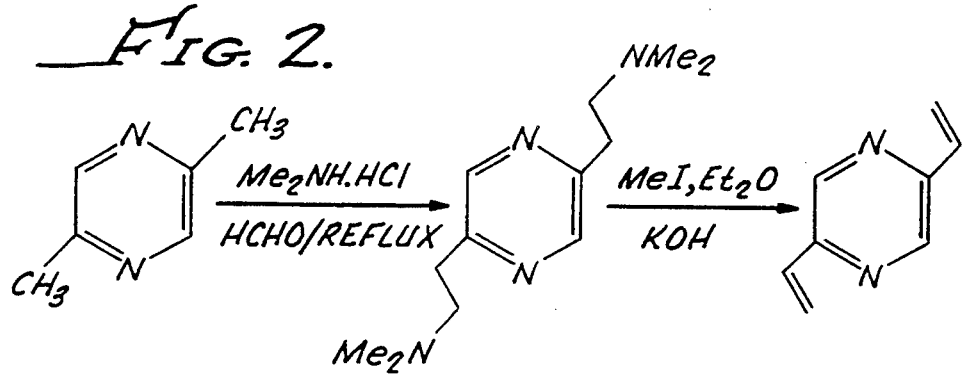
FIG. 2 illustrates a synthetic scheme for the synthesis of 2,5-divinylpyrazine, another of the novel cross-linkers of the present invention.

The preparation of 2,5-divinylpyrazine is similarly illustrated in FIG. 2. The cross-linker 2,5-divinylpyrazine was found to be slightly soluble in water.

Figure 3:
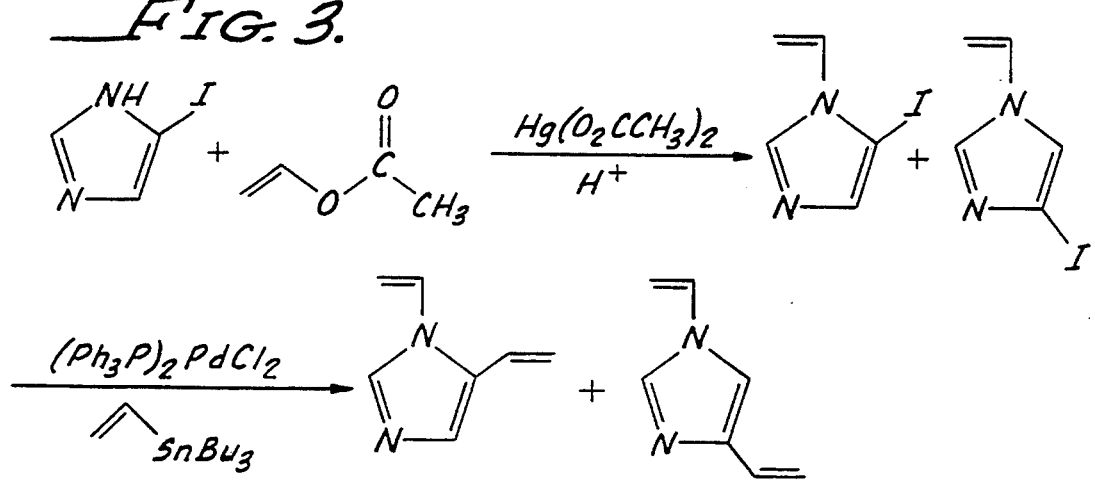
FIG. 3 illustrates a synthetic scheme for the synthesis of a mixture of 1,4-divinylimidazole and 1,5-divinylimidazole, which can also be used in the present invention.

Among other compounds which can be used in the present invention are the divinylimidazoles. For example, a mixture of 1,4-divinylimidazole and 1,5-divinylimidazole can be prepared, as illustrated in FIG. 3, wherein it can be seen that, in a two-step process, 4-iodoimidazole is reacted with vinyl acetate in an acidic suspension of mercuric acetate. Vinylation of the intermediates, 1-vinyl-4-iodoimidazole and 1-vinyl-5-iodoimidazole, results in the production of a mixture of 1,4-divinylimidazole and 1,5-divinylimidazole. The reagent used for the vinylation of the intermediates is a mixture of vinyltributylstannone and bis(triphenylphosphine)palladium(II) chloride. The mixture of 1,4-divinylimidazole and 1,5-divinylimidazole produced was found to be slightly soluble in water.

Generally, hydrogel-forming polymers are cross-linked polymers of water soluble or hydrophilic monomers or copolymers of water soluble and water insoluble comonomers. Because of their importance in the field of biomaterial and agriculture, hydrogels and processes for their formation are well documented in the literature. Heterocyclic compounds are especially preferred monomers and comonomers.

A preferred class of hydrogel forming polymers includes cross-linked polymers and copolymers of heterocyclic aromatic compounds such as 3-vinylpyridine, 4-vinylpyridine, 4-vinylpyrimidine, vinylpyrazine and 2-methyl-5-vinylpyrazine. Also preferred are copolymers of one or more of these comonomers with N-vinylimidazole or other heterocyclic compound such as N-vinyl-2-pyrrolidone and related N-alkenyl-2-pyrrolidones, N-vinyl carbazole, N-vinyl succinimide, N-(3-picolyl)methacrylamide, and 4-methyl-5-vinylthiazole. When cross-linked with the cross-linkers of the present invention, the resulting hydrogels have refractive indices, $n_D^{20}$, ranging from 1.54 to 1.60 in the dry state. They hydrate to a hydrated equilibrium water content ranging from about 40% to 90%. In the nitrogen containing heterocyclic aromatic compounds, the nitrogen atoms impart hydrophilicity via hydrogen bonding with water molecules, while the delocalization of the $\pi$ electrons of the aromatic rings contributes to the high refractive indices of the copolymers. Copolymers of nitrogen-containing heterocyclic aromatic compounds are therefore especially preferred.

As pointed out above, high water content hydrogels generally have very low refractive indices, $n_D^{20}$. It is, therefore, unexpected to find that a cross-linked polymer of vinylpyrazine, for example, with a very high equilibrium water content of 89.2% has a refractive index of 1.594. By using the high refractive index hydrogels of this invention it is possible to provide higher refractive power in a lens or other article with a much thinner optic portion than by using the low refractive index, high water content hydrogels previously available. It will be appreciated by those skilled in the art that the hydrogels of the present invention can be tailored to provide a wide range of refractive indices, $n_D^{20}$, upwards of about 1.570, and hydrated equilibrium water contents ranging from about 20% to 90%, in order to accommodate a variety of utilities.

The hydrogels of the present invention may also include from about 0.1 wt % to about 10 wt % ultraviolet (UV) radiation absorbing compounds. Preferably, the UV-absorbing compound is copolymerizable with the monomer forming the hydrogel polymer, thus becoming part of the final polymer or copolymer. This feature assures that the hydrated hydrogel is optically clear, and assures that the UV-absorbing compound does not leach or migrate from the article fabricated from the hydrogel, for example, from an implanted lens.

The following examples are offered as being illustrative of the principles of the present invention and not by way of limitation.

EXAMPLE 1

Synthesis of 4,6-Divinylpyrimidine

A quantity of 105 g of formalin was added dropwise to a mixture of 60 g of 4,6-dimethylpyrimidine and 104 g of dimethylamine hydrochloride in 82 ml of water at 130°–140° C. under stirring. Stirring was continued for 1.5 hours at 130°–135° C. after all the formalin had been added. The reaction mixture was cooled to room temperature and neutralized by adding a 30% sodium hydroxide solution to pH 12. Then, the product was extracted with 4×300 ml of methylene chloride. The combined organic layer was dried over anhydrous magnesium sulfate. After filtration and solvent removal, the intermediate, 4,6-bis(N,N-dimethylaminoethyl) pyrimidine, was vacuum distilled (114°–127° C./1.5 mm Hg, 82 g, 75%). Following isolation of the intermediate, 116 g of iodomethane was added dropwise to 82 g of the intermediate in 60 ml of ether at room temperature under stirring, and the mixture kept overnight without stirring. A quantity of 100 ml of water was added, the reaction mixture was warmed to 66°–75° C., and 80 ml of 30% sodium hydroxide solution was added under stirring, with stirring being continued for 20 minutes. The reaction was quenched by adding 150 ml of ice water. The mixture was extracted with 3×300 ml of methylene chloride. The combined organic layer was dried over anhydrous magnesium sulfate. Following filtration and solvent removal, the product, 4,6-divinylpyrimidine, was distilled under vacuum and found to be water miscible (50°–53° C./0.7 mm Hg, 37% $n_D$=1.569). $^1$H NMR (CDCl$_3$) δ 5.69 (2H, dd, J=10.5, 1.5 Hz), 6.47 (2H, dd, J=17.4, 1.5 Hz), 6.73 (2H, dd, J=17.4, 10.5 Hz), 7.21 (1H, d, J=1.2 Hz), 9.09 (1H, d, J=1.2 Hz); $^{13}$C NMR (CDCl$_3$) δ 114.98, 122.88, 135.13, 158.74, 162.80.

EXAMPLE 2

Synthesis of 2,5-Divinylpyrazine

The procedure of Example 1 was followed using 2,5-dimethylpyrazine as the starting material. The intermediate, 2,5-bis(N,N-dimethylaminoethyl)pyrazine, was prepared at a yield of 47% (118°–130° C./1.2 mm Hg). The product 2,5-divinylpyrazine was collected at 46°–50° C./1.2 mm Hg (36%, $n_D$=1.595). It was found to be slightly soluble in water. $^1$H NMR (CDCl$_3$) δ 5.57 (2H, dd, J=9.0, 1.2 Hz), 6.31 (2H, dd, J=17.7, 1.2 Hz), 6.80 (2H, dd, J=17.7, 9.0 Hz), 8.51 (2H, s); $^{13}$C NMR (CDCl$_3$) δ 120.18, 133.27, 142.31, 149.38.

EXAMPLE 3

Synthesis of 1,4-Divinylimidazole and 1,5-Divinylimidazole

To a suspension of 5 g of mercuric acetate in 250 ml of vinyl acetate and 150 ml of carbon tetrachloride was added a solution of 0.5 ml of concentrated sulfuric acid in 15 ml of ethyl acetate. After the mercuric acetate had dissolved, 20 g of 4-iodoimidazole was added under an inert atmosphere. The reaction suspension was stirred at 50° C. for 5 hours. Following filtration and solvent removal, the intermediate compounds were purified by column chromatography (1:1 ethyl acetate/hexane). A yield of 15 g of a mixture of N-vinyl-4-iodoimidazole and N-vinyl-5-iodoimidazole was collected (66%). Next, a mixture of 15 g of the intermediate mixture, 23.8 g of vinyltributylstannone, and 2.8 g of bis(triphenylphosphine)palladium(II) chloride in 180 ml of 1,2-dichloroethane was stirred at 85°–90° C. for 6 hours. The reaction mixture was cooled to room temperature and diluted with 300 ml of ether. Then 12 g of potassium fluoride was added. The product was purified by column chromatography (3:10 ethyl acetate/hexane) and further purified by distillation (68°–70° C./2 mm Hg, 55%, $n_D$=1.560). The product mixture of 1,4-divinylimidazole and 1,5-divinylimidazole was found to be slightly soluble in water. $^1$H NMR (CDCl$_3$) δ 4.86 (1H, dd), 5.06 (1H, dd), 5.18 (1H, dd), 5.23 (1H, dd), 5.27 (1H, dd), 5.38 (1H, dd), 5.58 (1H, dd), 5.87 (1H, dd), 6.52 (1H, dd), 6.58 (1H, dd), 6.82 (1H, dd), 6.87 (1H, dd), 7.10 (1H, s), 7.15 (1H, s), 7.57 (1H, s), 7.67 (1H, s); $^{13}$C NMR (CDCl$_3$) δ 103.00, 106.50, 112.80, 113.54, 116.00, 122.75, 127.84, 128.08, 128.60, 129.20, 130.16, 135.55, 136.45, 141.80.

The following example illustrates the use of the cross-linkers of the present invention in comparison with previously used cross-linkers in the preparation of hydrogels.

EXAMPLE 4

A total of seven different copolymers was prepared and evaluated for use as exemplary hydrogel forming materials. Table I illustrates the proportions of each component of the polymerization mixture, the cross-linker used, and the properties of the cross-linked copolymers. Each polymerization procedure was carried out by first mixing the appropriate amounts of the co-monomers and cross-linker, as indicated in Table I, with 2,2'-azobisisobutyronitrile as a polymerization initiator. Then each mixture was transferred to an ampoule which was pretreated with a silicone grease mold releasing agent. Each ampoule and mixture was then attached to a vacuum system and cooled with liquid nitrogen. After the mixture was frozen by the liquid nitrogen, the mixture was evacuated by turning on the vacuum system. Once a constant pressure was achieved, the vacuum system was turned off and the mixture was allowed to thaw by warming the ampoule in a water bath. This freeze-thaw cycle was repeated three times in order to provide sufficient mixture degassing. Finally, each mixture and ampoule were sealed under vacuum or an inert gas such as nitrogen or argon and polymerized at a temperature of 60° C. for a period of 36 hours, then at 135° C. for 12 hours.

The abbreviations utilized in Table I are identified in Table II, immediately following.

TABLE I

| HYDROGEL | COMONOMERS | CROSS-LINKER | PROPERTIES |
| --- | --- | --- | --- |
| 1 | NVI (49%)$^a$<br>VPM (30%)<br>4VP (20%) | DVB (1%) | Opaque<br>59% Water |
| 2 | NVI (49%)<br>VPM (30%) | DEGDA (1%) | Transparent<br>67% Water |

TABLE I-continued

| HYDROGEL | COMONOMERS | CROSS-LINKER | PROPERTIES |
|---|---|---|---|
| | 4VP (20%) | | $n_D^{20}$ 1.586 |
| 3 | NVI (49%) | DVI (1%) | Transparent |
| | VPM (30%) | | 67% Water |
| | 4VP (20%) | | |
| 4 | NVI (49%) | DVPM (1%) | Transparent |
| | VPM (30%) | | 64% Water |
| | 4VP (20%) | | |
| 5 | VPM (33.7%) | DVPM (1.3%) | Transparent |
| | NVI (30%) | | 68% Water |
| | NVP (20%) | | $n_D^{20}$ (dry) = 1.57 |
| | 4VP (15%) | | $n_D^{37}$ (hydrated) = 1.41 |
| 6 | VPM (30.2%) | DVPM (0.8%) | Transparent |
| | NVI (30%) | | 68% Water |
| | NVP (20%) | | $n_D^{20}$ (dry) = 1.57 |
| | 4VP (15%) | | $n_D^{37}$ (hydrated) = 1.40 |
| | VMT (4%) | | |
| 7 | VPM (81.7%) | DVPM (0.3%) | Transparent |
| | VMT (18%) | | 70% Water |
| | | | $n_D^{20}$ (dry) = 1.57 |
| | | | $n_D^{37}$ (hydrated) = 1.41 |

*a*Mole percentage

TABLE II

| COMPONENT | ABBREVIATION |
|---|---|
| N-vinylpyrrolidone | NVP |
| N-Vinylimidazole | NVI |
| 4-Vinylpyridine | 4VP |
| Diethylene glycol diacrylate | DEGDA |
| 4-Vinylpyrimidine | VPM |
| Divinylbenzene | DVB |
| 1,4(5)-Divinylimidazole (a mixture of 1,4-divinylimidazole and 1,5-divinylimidazole) | DVI |
| 4,6-Divinylpyrimidine | DVPM |
| 4-methyl-5-vinylthiazole | VMT |

The following example illustrates the relative stability of hydrogels prepared using the cross-linkers of the present invention compared with a hydrogel prepared using a previously available cross-linker which is hydrophilic but hydrolyzable.

EXAMPLE 5

Figure 4:
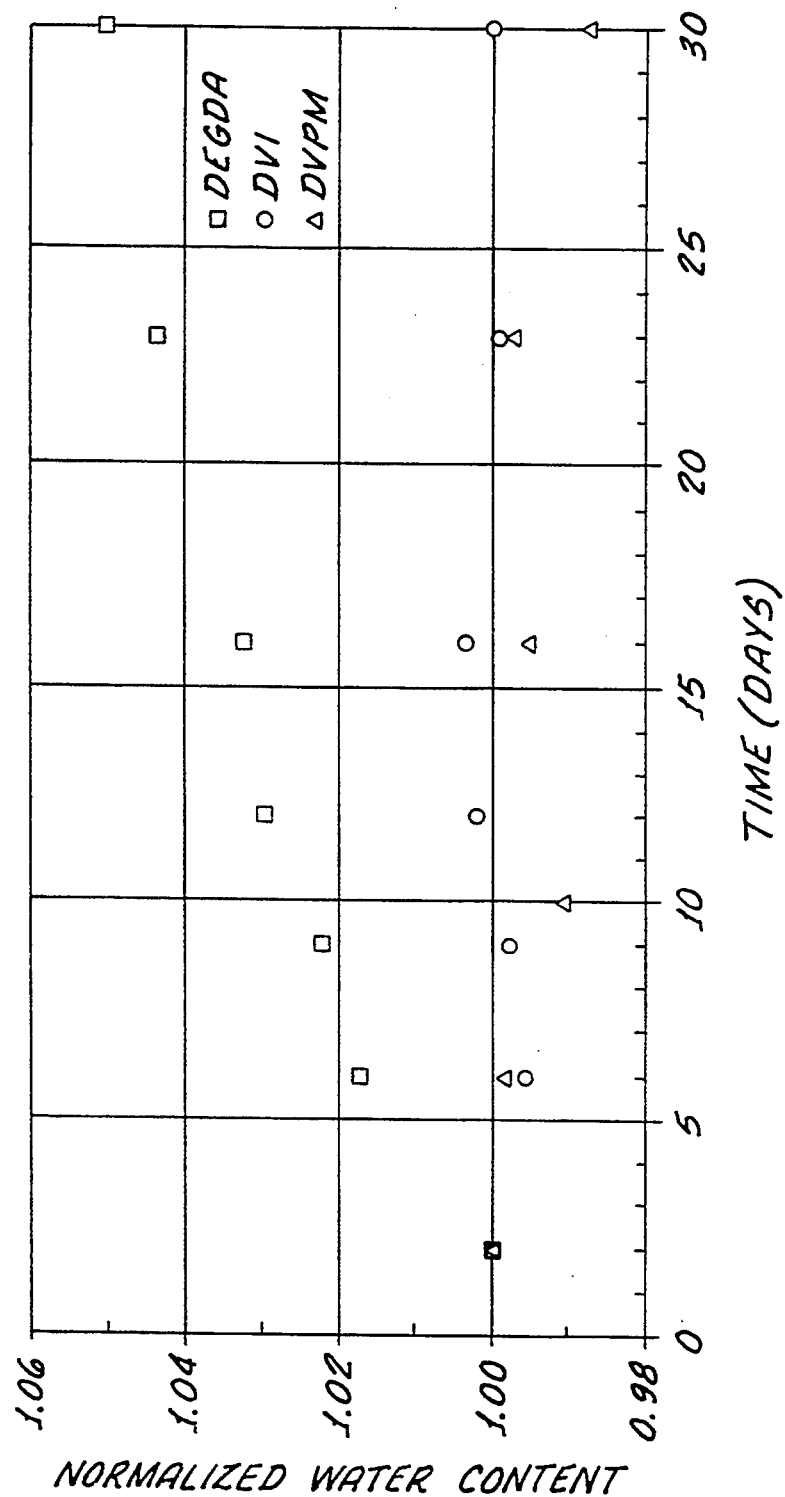
FIG. 4 is a graphical representation of the change in water content of various cross-linked hydrogels over an extended period of time.

The water contents of hydrogels (2), (3) and (4) of Table I of Example 4 were determined initially and at periods of 2, 6, 9, 10, 12, 16, 23 and 30 days. Hydrogel (2) was cross-linked with diethyleneglycol diacrylate (DEGDA), a hydrophilic but hydrolyzable cross-linker. Hydrogel (3) was cross-linked with 1,4(5)-divinylimidazole (DVI), a hydrophilic and non-hydrolyzable cross-linker according to the present invention. Hydrogel (4) was cross-linked with 4,6-divinylpyrimidine (DVPM), a novel hydrophilic and non-hydrolyzable cross-linker according to the present invention. The results are plotted in FIG. 4.

It can be seen that, with the passage of time, the water content of the hydrogel cross-linked with DEGDA, a hydrophilic but hydrolyzable cross-linker, continuously increases whereas the water contents of hydrogels cross-linked with DVI or DVPM, hydrophilic and non-hydrolyzable cross-linkers according to the present invention, show substantially no increase in water content. The increase in water content of the DEGDA cross-linked hydrogel indicates continuous loss of polymer. Since no loss of polymer over time is observed for the DVI cross-linked hydrogel or the DVPM cross-linked hydrogel, the stability of these hydrogels is markedly improved over that of the DEGDA cross-linked hydrogel.

Because of the outstanding properties of hydrogels produced using the hydrophilic non-hydrolyzable cross-linkers of the present invention including their optical transparency, their high water content, and their high refractive index, they display extremely good optical resolution efficiency.

Thus, the use of the hydrophilic, non-hydrolyzable cross-linkers of the present invention results in hydrogels which display excellent optical properties, as well as excellent stability.

Having thus described exemplary embodiments of the present invention, it should be noted by those skilled in the art that the disclosures herein are exemplary only and that alternatives, adaptations, and modifications may be made within the scope of the present invention.

What is claimed is:

1. A hydrogel comprising a copolymer cross-linked with a non-hydrolyzable, hydrophilic cross-linking agent selected from the group consisting of 4,6-divinylpyrimidine, 2,5-divinylpyrazine, 1,4-divinylimidazole, and 1,5-divinylimidazole.

2. The hydrogel of claim 1 wherein said copolymer is a copolymer of at least two comonomers selected from the group consisting of 3-vinylpyridine, 4-vinylpyridine, 4-vinylpyrimidine, vinylpyrazine, and 2-methyl-5-vinylpyrazine.

3. The hydrogel of claim 1 wherein said copolymer is a copolymer of at least one comonomer selected from the group consisting of 3-vinylpyridine, 4-vinylpyridine, 4-vinylpyrimidine, vinylpyrazine, and 2-methyl-5-vinylpyrazine; and at least one comonomer selected from the group consisting of N-vinyl-2-pyrrolidone, N-vinyl carbazole, N-vinylsuccinimide, N-(3-picolyl)-methacrylamide, and 4-methyl-5-vinylthiazole.

4. The hydrogel of claim 1 having a refractive index $n_D^{20}$ of about 1.540 to 1.594 in the dry state.

5. The hydrogel of claim 1 having a hydrated equilibrium water content of about 40% to 90%.

6. The hydrogel of claim 1 wherein said copolymer is a copolymer of N-vinylimidazole, 4-vinylpyrimidine, and 4-vinylpyridine.

7. The hydrogel of claim 1 wherein said copolymer is a copolymer of 4-vinylpyrimidine, N-vinylimidazole, N-vinyl-2-pyrrolidone, and 4-vinylpyridine.

8. The hydrogel of claim 1 wherein said copolymer is a copolymer of 4-vinylpyrimidine, N-vinylimidazole, N-vinyl-2-pyrrolidone, 4-vinylpyridine, and 4-methyl-5-vinylthiazole.

9. The hydrogel of claim 1 wherein said copolymer is a copolymer of 4-vinylpyrimidine and 4-methyl-5-vinylthiazole.

* * * * *